United States Patent [19]

Acosta

[11] Patent Number: 4,996,310

[45] Date of Patent: Feb. 26, 1991

[54] POLYOL-POLYETHER WITH HIGH CONTENT OF ETHYLENE OXIDE AND LOW VISCOSITY

[75] Inventor: Roberto M. Acosta, Toluca, Mexico

[73] Assignee: Polioles, S. A. de C.U., Col. Condesa, Mexico

[21] Appl. No.: 321,786

[22] Filed: Mar. 10, 1989

[51] Int. Cl.$^5$ .................... C07H 15/00; C07H 1/00; C07H 3/00; C07C 43/00; A61K 31/00

[52] U.S. Cl. ........................... 536/120; 536/124; 536/1.1; 568/606; 568/620; 514/53; 514/54

[58] Field of Search ............... 536/120, 124, 1.1; 568/606, 620

[56] References Cited

U.S. PATENT DOCUMENTS

| | | | |
|---|---|---|---|
| 2,902,478 | 9/1959 | Anderson | 536/120 |
| 3,153,002 | 10/1964 | Wismer et al. | 521/131 |
| 3,277,076 | 10/1966 | Yotsuzuka | 536/120 |
| 3,369,014 | 2/1968 | Booth | 536/120 |
| 4,166,172 | 8/1979 | Klein | 536/120 |
| 4,230,824 | 10/1980 | Nodelman | 536/120 |
| 4,385,173 | 5/1983 | Dix et al. | 536/120 |
| 4,446,313 | 5/1984 | Dix et al. | 536/120 |

FOREIGN PATENT DOCUMENTS

| | | | |
|---|---|---|---|
| 47-48366 | 12/1972 | Japan | 536/120 |
| 63-241028 | 10/1988 | Japan | 536/120 |

*Primary Examiner*—Ronald W. Griffin
*Assistant Examiner*—Everett White
*Attorney, Agent, or Firm*—Timmons & Kelly

[57] ABSTRACT

There is described and claimed a polyol-polyether having a high content of ethylene oxide and low viscosity, greatly suitable for use in the preparation of rigid polyurethane foam.

The polyol-polyether of this invention is of high quality and low cost, as well as having low viscosity, thus expediting handling in foaming machines.

12 Claims, No Drawings

POLYOL-POLYETHER WITH HIGH CONTENT OF ETHYLENE OXIDE AND LOW VISCOSITY

BACKGROUND OF THE INVENTION

Polyols or polyhydroxyl alcohols are chemical compounds which contain various oxyhydryl or hydroxyl groups (—OH) in their molecules. They are also known as polyalcohols and in an abbreviated form, precisely polyols.

These polyols are important in the industrial application of polyurethane foams and, depending on their particular characteristics, such as functionality, oxyhydryl number and molecular weight, find specific uses in the production of said foams to impart to the same flexibility, rigidity, elasticity, etc.

It is well known that in order to produce polyols industrially it is necessary to begin with an alcohol with a given group of oxyhydryls per mol. The alcohol is reacted with an alkylene oxide under certain conditions of catalysis, temperature, pressure and time. Further, in order to produce rigid polyurethane foams it is necessary to employ a polyol with a function greater than three. Therefore, the alcohols employed to produce a polyol must have a high function in order to admix and react with the alkylene oxides and obtain a functionality greater than three.

However, some of the most used alcohols, having polyfunctions are solids at ambient temperature and inclusive at reaction temperatures (between 80 and 130 degrees C.). Trimethylolpropane, pentaerythritol, sorbitol, sucrose, etc. are some of the examples of these alcohols.

Upon requiring a greater function, it is necessary to employ materials such as sorbitol and sucrose. The temperatures of fusion of these materials are very high and normally close to their temperature of decomposition, all of which makes handling the materials difficult.

Since some time before, processes have been developed for obtaining polyether from polyols by reacting alkylene oxide with sucrose. The principal part of these processes is the handling of the sucrose during the process for obtaining the polyol.

Some processes are described in the literature involving the reaction of the sucrose with alkylene oxide in volume. This reaction has the advantage that products of high function (7-8) are obtained and that the reaction time is short. In this way the sucrose is suspended in the alkylene oxide. However, in this way polyols with high viscosity normally between 40,000 and 400,000 centipoises at ambient temperature, are obtained. This is not practical since problems are caused in the handling of the polyol in normal foaming machines. Also, there is a risk represented by handling large quantities of alkylene oxide within the reactors at the reaction temperature due to the high vapor pressure, which makes this highly explosive.

Other processes are also known, involving the use of inert solvents such as toluene, xylene or benzene which dissolve the sucrose and expedite the oxyalkylation thereof, thus reducing the yield due to the use of 10 to 40% of the solvent.

Also, other processes exist where the sucrose is diluted in alcohols which react at the same time with the alkylene oxides. One of the most common is water which upon reacting forms oxyalkyl compounds with a function of two and which are harmful to the production of rigid polyurethane. Some other alcohols used are monoethylene glycol, monopropylene glycol, triethanolamine, glycerine, ethylenediamine, etc.

In all the known processes alkylene oxides are used. Propylene oxide is the most common alkylene oxide used and only in a few processes is use made of ethylene oxide in amounts up to 40%.

U.S. Pat. No. 3,153,002 includes examples wherein the content of ethylene oxide amounts up to 65%, using water to dilute the sucrose and carrying out the reaction at a very low temperature, up to 43 degrees C.

U.S. Pat. No. 2,902,478 includes an example wherein the content of ethylene oxide amounts to 47%, the reaction being initiated in mass and at a pressure of 155 psig which evidently is very dangerous. Also a high viscosity is obtained, which is undesirable.

As is evident from the above, there is a need for a practical, effective and convenient product of low viscosity and high content of ethylene oxide which does not have the disadvantages of the products previously mentioned.

OBJECTS OF THE INVENTION

It is a main object of this invention to provide a polyolpolyether starting from sucrose with a very high content of ethylene oxide by a process which is greatly effective and advisable to carry out.

Another object of this invention resides in furnishing a low viscosity polyol-polyether starting from sucrose.

Yet another object of this invention resides in furnishing a polyol-polyether that may be employed in the preparation of rigid polyurethanes. This new polyol is of high quality and low cost and due to its high content of ethylene oxide and its low viscosity expedites handling in foam making machines.

Other objects and advantages of this invention will be evident from the following description thereof.

DETAILED DESCRIPTION OF THE INVENTION

Hereinafter the invention will be described in detail, the novel product being prepared in a reactor charged with a triol which may be glycerine, trimethylolpropane or triethanolamine. In the event that glycerine or triethanolamine is used charging of the reactor is performed at a temperature approximately between 10 and 30 degrees C., and in the event that trimethylolpropane is used, the same is charged into the reactor at a temperature of 70 degrees C.

Once the reactor has been charged with the triol, stirring of the contents is begun.

Thereafter, the reactor is charged with sucrose which may be added at a temperature between 20 and 70 degrees C., approximately. This charges may be carried out by mechanical or manual means.

Immediately following, the catalyzer is charged. The catalyzer is preferably sodium hydroxide, potassium hydroxide or an alkylamine, e.g., trimethylamine, triethylamine or tributylamine.

The entire admixture contained in the reactor is stirred for a period between 30 minutes and two hours during which heating is initiated at a temperature between 85 and 135 degrees C. In this way a homogeneous mixture is obtained, suitable for being easily oxyalkylized.

Then, the addition of the propylene oxide is begun at an initial pressure of 10-0 psig and at a temperature between 100 and 120 degrees C. approximately, for a period between 3 and 4 and a half hours, approximately.

Upon concluding the addition the reaction is left to proceed for a period of 2 to 3 hours approximately at a temperature between 85 and 135 degrees C.

The product is then cooled to 60 degrees C. approximately. Then, charging of the second portion of sucrose begins, maintaining the reactor under agitation. The mixture is stirred during a period from 1 to 4 hours approximately, during which the mixture is heated at a temperature between 105 and 140 degrees C. In this way, the first portion which is oxypropylated serves as a means for dissolving the second portion of sucrose, expediting the oxyethylation.

Following the above, the addition of ethylene oxide is begun, being carried out during a period between 8 and 14 hours at a temperature comprised from 120 to 130 degrees C. and under a nitrogen pressure between 34 to 90 psi inside the reactor. Once the addition of the ethylene oxide is terminated, the reaction of the mixture is left to proceed between 2 and 4 hours at a temperature between 105 and 140 degrees C. approximately. The material thus obtained is substantially free from solid sucrose.

Finally, the catalyzer in the product is neutralized by the addition of an acid in aqueous solution, preferably phosphoric, sulfuric, acetic acid, etc., at a concentration between 25 and 100%. The catalyzer may be eliminated also by an ion exchange with magnesium silicate and subsequently filtering the product, to eliminate the salts and solids present.

For the purpose of illustrating clearly the preferred embodiments of the invention various specific examples of the novel product of the invention follow.

EXAMPLE 1

In a reactor equipped with a heating system, cooling coil, agitator and supplementary equipment 737 g of triethanolymine are charged at a temperature of 25 degrees C. approximately, the stirring being initiated at 80 rpm approximately.

Later, 500 g of sucrose and 23.4 g of tributylamine are added. The reactor is closed and the air within is purged by means of nitrogen. The reactor is heated to 110 degrees C. and 1080 g of propylene oxide are added. The maximum pressure developed was 34 psig, without significant exterior heating or cooling. Once the addition is terminated, the propylene oxide present is reacted until such time as no considerable variation in the interior pressure of the reactor exists. The mixture is cooled to 60 degrees C. and 1524 g of sucrose and 737 g of triethanolamine are charged into the reactor, with stirring being maintained all the time. The reactor is closed and heated to a temperature of 120 degrees C. which is obtained during a period of 2 hours. The pressure is adjusted to 34 psig approximately with nitrogen. Then 4260 gl of ethylene oxide are added during a period of 10 hours and at a pressure of less than 90 psig, approximately. Once the addition is terminated the charge is reacted at 125 degrees C. for 1.5 hours for the purpose of reacting the ethylene oxide yet present in the admixture.

In this manner, a polyol-polyether is obtained which submitted to analysis gave the following results:

| Gardner color | 40 |
| pH | 10 |
| % H$_2$O | 0.055 |
| Oxyhydryl No. | 525 |
| Viscosity mps 25 degrees C. | 2500 |
| % Ethylene oxide | 47.3 |
| Functionality | 4.5 |

EXAMPLE 2

In the same reactor mentioned in Example No. 1, 313 g of glycerine, 316 g of sucrose and 50 g of a 50% solution of Potassium hyudroxide are charged. The mixture was stirred for 2 hours. During such period the mixture was heated to a temperature of 112 degrees C. and the air was purged by means of nitrogen bubbling, leaving a pressure of 2 psig with the nitrogen. Later, 900 g of propylene oxide were added during a period of 4 hours and at a temperature of 112 degrees C. The maximum pressure reached was 90 psig approximately and the heating and stirring were continued after terminating the addition for a period of 2 hours. Later, the admixture was cooled to 60 degrees C. and 957 g of sucrose and 311 g of glycerine were charged. The reactor was closed and the air purged with nitrogen, the mixture being heated to 120 degrees C. obtained within a period of 2 hours and adjusting the pressure to 34 psig approximately 6781 g. of ethylene ,oxide are added during a period of 12 hours and at a pressure not greater than 90 psig approximately. Once the addition is terminated the mixture is allowed to react for a period of time sufficient until no significant changes exist in the interior of the reactor. Later, the product is treated with magnesium silicate and filtered for 2 hours at a temperature of 90 degrees C. and filtered through a screen at a pressure of 29 psig approximately.

Once the solids are separated from the product, the volatile products and humidity are eliminated at a temperature of 110 degrees C. approximately by the use of vacuum.

In this manner a polyol-polyether is obtained, which submitted to analysis offers the following results:

| Gardner color | 10 |
| pH | 9.0 |
| % H$_2$O | 0.011 |
| Oxyhydryl No. | 310 |
| Viscosity mps 25 degrees C. | 630 |
| % Ethylene oxide | 70 |
| Functionality | 4.4 |

Although the invention has been described with respect to the preferred embodiments, it must be understood that the same are illustrative and not limiting in any manner. Further, it must be understood that the invention is susceptible of modifications and variations, as may be considered falling within the scope of the invention, to be limited only by the claims inserted hereinafter.

What is claimed is:

1. A polyol-polyether having a molecular weight between 400 and 900, a viscosity between 500 and 3500 centipoises at 25 degrees C., and a content of ethylene oxide between 40% and 75% by weight, prepared by a process which comprises the steps of:
   (a) forming a suspension of sucrose in a triol;
   (b) reacting the mixture obtained in the prior step with propylene oxide in the presence of a catalyzer;

(c) suspending sucrose in the mixture obtained in the prior step;

(d) oxyethylizing the mixture of step (c); and (e) eliminating the volatile components of the mixture and the catalyzer, thus obtaining the desired polyol-polyether.

2. The product in accordance with claim 1, wherein the triol of step (a) is selected from a group consisting of glycerine, trimethylolpropane or triethanolamine.

3. The product of claim 1, wherein the catalyzer used in step (b), is selected from a group consisting of sodium hydroxide, potassium hydroxide or an alkylamine.

4. The product in accordance with claim 3, wherein the alkylamine is selected form a group consisting of triethylamine, trimethylamine or tributylamine.

5. The product in accordance with claim 1, wherein step (a) is carried out by heating at a temperature between 85 and 135 degrees C., with stirring, for a period between 0.5 hour and 2 hours.

6. The product in accordance with claim 1, wherein step (b) is carried out at an initial nitrogen pressure between 10 and 0 psig and at a temperature between 110 and 120 degrees C. during a period of 3 to 4.5 hours.

7. The product in accordance with claim 1, wherein step (c) is carried out at a temperature between 105 and 140 degrees C.

8. The product in accordance with claim 1, wherein step (c) is carried out by the addition of ethylene oxide at a temperature between 120 and 130 degrees C. under a nitrogen pressure between 34 and 90 psig, during a period of 8 to 14 hours.

9. The product in accordance with claim 1, wherein step (e) is carried out by neutralizing the catalyzer by adding an acid in aqueous solution at a concentration between 25 and 100% by weight.

10. The product in accordance with claim 9, wherein the acid is selected from a group consisting of phosphoric, sulfuric or acetic acid.

11. The product in accordance with claim 1, wherein step (e) is carried out by ion exchange of the catalyzer with a magnesium silicate and later filtration of the product to eliminate salts and solids present therein.

12. A polyol-polyether having a molecular weight between 400 and 900, a viscosity between 500 and 3500 centipoises at 25 degrees C. and a content of ethylene oxide between 40 and 75% by weight.

* * * * *